United States Patent [19]

Houts et al.

[11] Patent Number: 4,757,004

[45] Date of Patent: Jul. 12, 1988

[54] CHROMATOGRAPHIC DEVICES HAVING MODIFIED EDGES

[75] Inventors: Thomas M. Houts, Mountain View; Edwin F. Ullman, Atherton, both of Calif.

[73] Assignee: Syntex (U.S.A.) Inc., Palo Alto, Calif.

[21] Appl. No.: 591,155

[22] Filed: Mar. 16, 1984

[51] Int. Cl.$^4$ ............................................. G01N 33/53
[52] U.S. Cl. ........................................ 435/7; 162/194;
162/260; 162/286; 210/198.2; 210/456;
219/121.69; 219/212.72; 219/121.74;
219/121.8; 422/56; 422/70; 422/71; 427/3;
435/803; 435/805; 436/528; 436/161; 436/162;
436/810
[58] Field of Search ............................ 435/7, 803, 805;
436/528, 161, 162, 169, 810, 824; 422/56, 70,
71; 210/456, 190.2; 162/194, 286, 260; 427/3;
219/121 LG, 121 LN, 121 LQ, 121 LW

[56] References Cited

U.S. PATENT DOCUMENTS

| | | | |
|---|---|---|---|
| 4,235,601 | 11/1980 | Deutsch et al. | 436/810 |
| 4,430,549 | 2/1984 | Macken | 219/121 LG |
| 4,435,504 | 3/1984 | Zuk et al. | 436/162 |

*Primary Examiner*—Christine M. Nucker
*Attorney, Agent, or Firm*—Theodore J. Leitereg; Carole F. Barrett

[57] ABSTRACT

A device is disclosed for use in a chromatographic system wherein a component of a mixture is partioned between a liquid phase and an immobile phase. The device is comprised of a chromatographic material. In the chromatographic system the component traverses at least a portion of the chromatographic material. The device generally has at least one longitudinal edge substantially corresponding to the direction of traverse of the component. The longitudinal edge includes means for controlling the shape of the front of the traversing component.

20 Claims, 5 Drawing Sheets

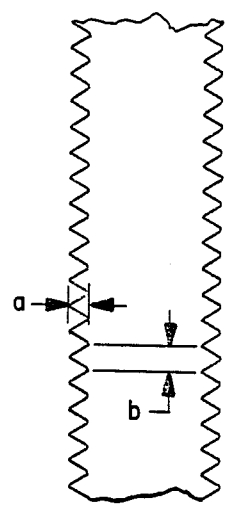
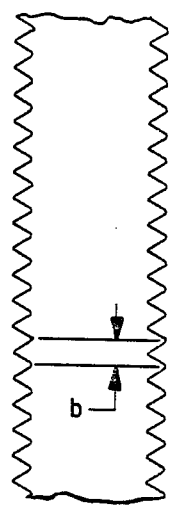
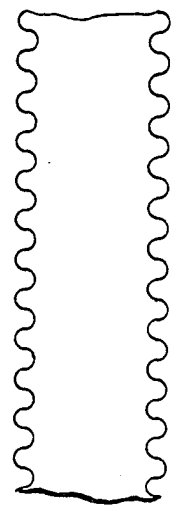
FIG. 1  FIG. 2  FIG. 3
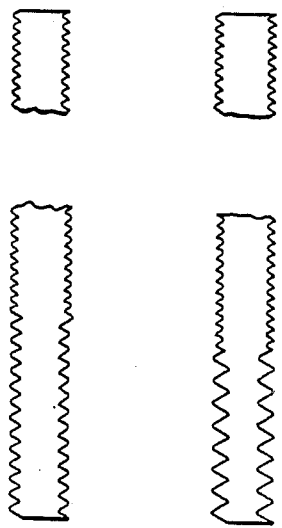
FIG. 4

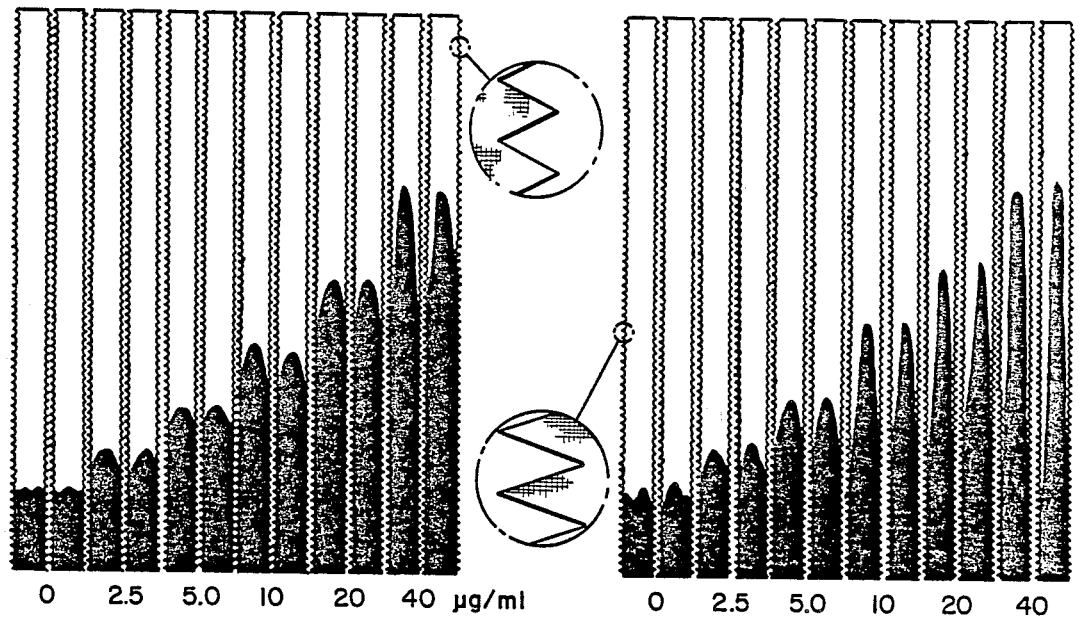
FIG. 9
FIG. 10
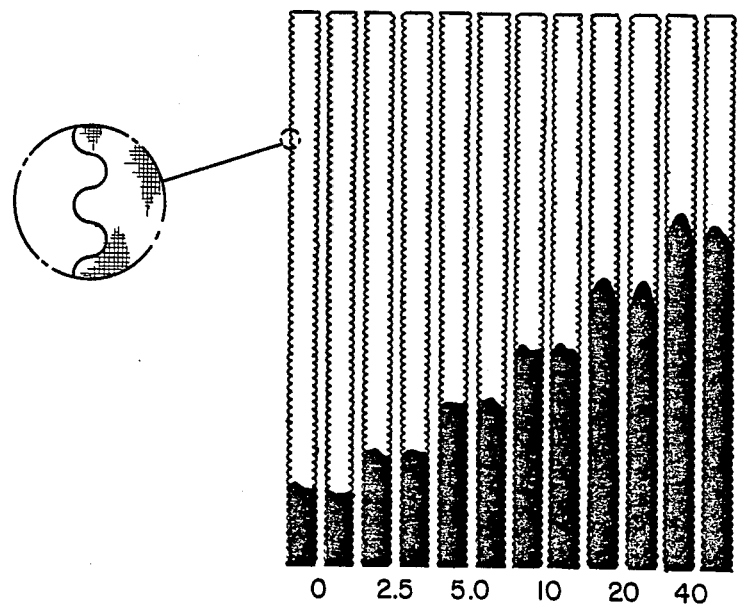
FIG. 11

CHROMATOGRAPHIC DEVICES HAVING MODIFIED EDGES

BACKGROUND OF THE INVENTION

1. Field of the Invention

This invention relates to improved chromatographic devices and methods of preparing them. The improved chromatographic devices of the invention are useful in analytical chromatography, particularly in immunochromatography.

A number of materials are known for use as chromatographic media. Generally, the material is "bibulous" or "porous," such as that found in a random or oriented pile of fibers of cellulose, fiberglass, etc., in powdered silica, and the like. Chromatographic material is generally used in a chromatographic device, wherein the material is traversed by a component of a mixture. The component is generally in equilibrium with a mobile phase, usually a liquid medium, most usually a solvent.

Devices in which chromatographic material is employed take many forms. For example, the device may be a strip cut from a sheet of bibulous material, e.g., paper. On the other hand, the device may be a support on which a chromatographic material is contained. Exemplary of the latter is a chromatographic plate which contains, e.g., silica or the like.

Chromatographic strips are normally prepared from larger sheets from which they are cut by mechanical means. The most widely used form of mechanical cutting involves at least one blade or wire.

Mechanical cutting of the sheet into strips results in a deformation of the edge of the strip along the cutting line. This deformation takes the form of a compression of the edges of the strip by the blade or wire. In fibrous strips the fibers which form the strip are pushed closer together at the edges when compared to the distance between the fibers in the body of the strip. This deformation of the edges of the strip frequently results in a faster rate of traversal for the mobile phase at the edges of the strip than through the body of the strip. The front of the mobile phase and other components traversing the strip becomes concave rather than flat.

In many situations in which a chromatographic device is employed, it is important that the shape of the front formed by a component of a mixture traversing the chromatographic material be controlled. In analytical chromatography it is usually preferable to have a flat or convex front whereas in preparative chromatography a flat front is required. An example of such a situation is affinity chromatography in which antibodies are attached to a porous insoluble support. During migration of an antigen-containing solution on the porous support, migration of the antigen solute is specifically delayed in comparison to the migration of the solvent and other solutes. The relative delay decreases with increasing antigen concentration. Accurate quantitation of the concentration of analyte in a sample to be analyzed requires that the position of the analyte front relative to the solvent front be measured accurately. The position of a flat or convex front can usually be measured with greater precision and accuracy than that of a concave front, and a higher degree of accuracy could thereby be obtained in a chromatographic assay. Moreover, in preparative chromtography a linear front permits more ready separation and isolation of the pure conponent.

2. Brief Description of the Prior Art

U.S. Pat. No. 4,168,146 describes an immunoassay employing immunochromatography with antigens followed by contacting the immunochromatograph with an aqueous solution containing labelled antibodies. An enzyme chromtographic immunoassay is described in U.S. Ser. No. 398,505, filed July 15, 1982, now U.S. Pat. No. 4,434,504.

SUMMARY OF THE INVENTION

The device of the present invention is comprised of a chromatographic material. The device is useful in a chromatographic system wherein a component of a mixture is partitioned between a liquid phase and an immobile phase and the component traverses at least a portion of the chromatographic material. The device generally has at least one longitudinal edge that comes in contact with the traversing component during the chromatographic process and that lies in a direction substantially corresponding to the direction of traverse. The longitudinal edge includes a means for controlling the shape of the front of the traversing component by reducing the rate of migration near the edge. In one embodiment, the device of the present invention contains a plurality of indentations along its longitudinal edge. The number, size and configuration of the indentations provide means for control of the configuration of the front of the traversing component. In another embodiment, the longitudinal edge is chemically treated to reduce the rate of migration of the traversing component near the edge.

BRIEF DESCRIPTION OF THE DRAWING

FIG. 1 depicts a chromatographic device in accordance with the present invention wherein the longitudinal edges of the device have triangular indentations which are in phase. The amplitude of the indentations is designated by the letter "a". The wavelength of the indentations is designated by the letter "b."

FIG. 2 depicts a chromatographic device similar to FIG. 1 except that the indentations are out of phase rather than in phase.

FIG. 3 depicts a chromatographic device similar to FIG. 1 except that the indentations are semi-circular rather than triangular.

FIG. 4 depicts chromatographic devices in accordance with the present invention wherein the amplitude and wavelength of the indentations at the bottom portion differ from that at the top portion of the devices.

FIGS. 5–11 depicts the results of immunochromatographic assays employing chromatographic devices in accordance with the present invention.

DESCRIPTION OF THE SPECIFIC EMBODIMENTS

Figures 5, 6:
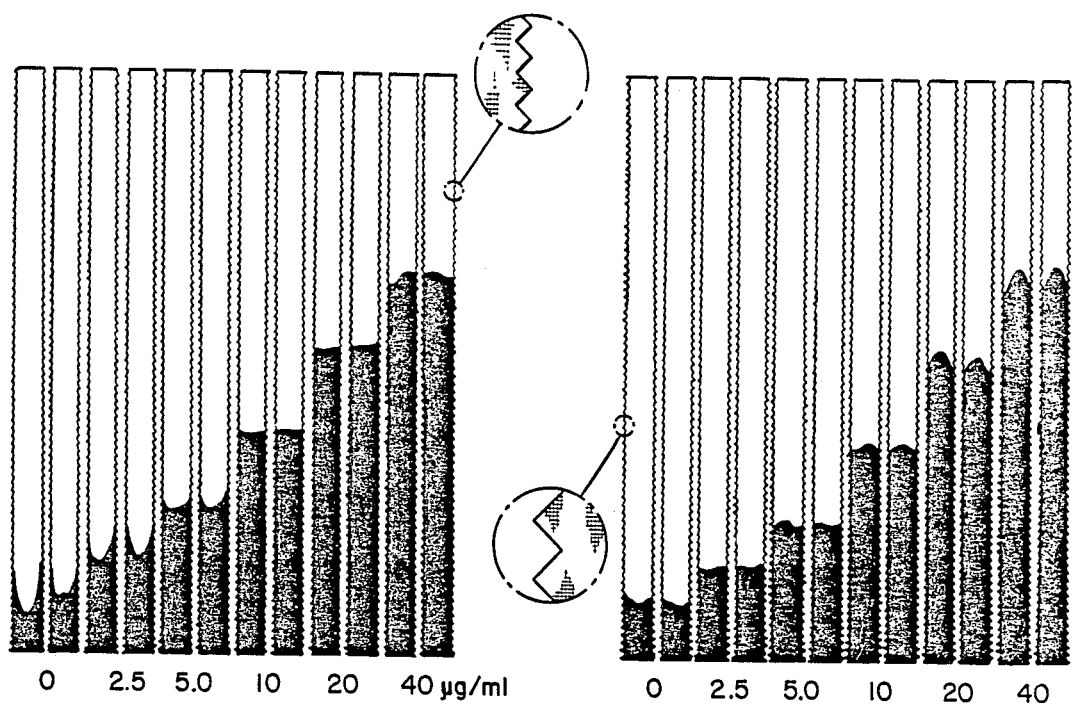
Figures 7, 8:
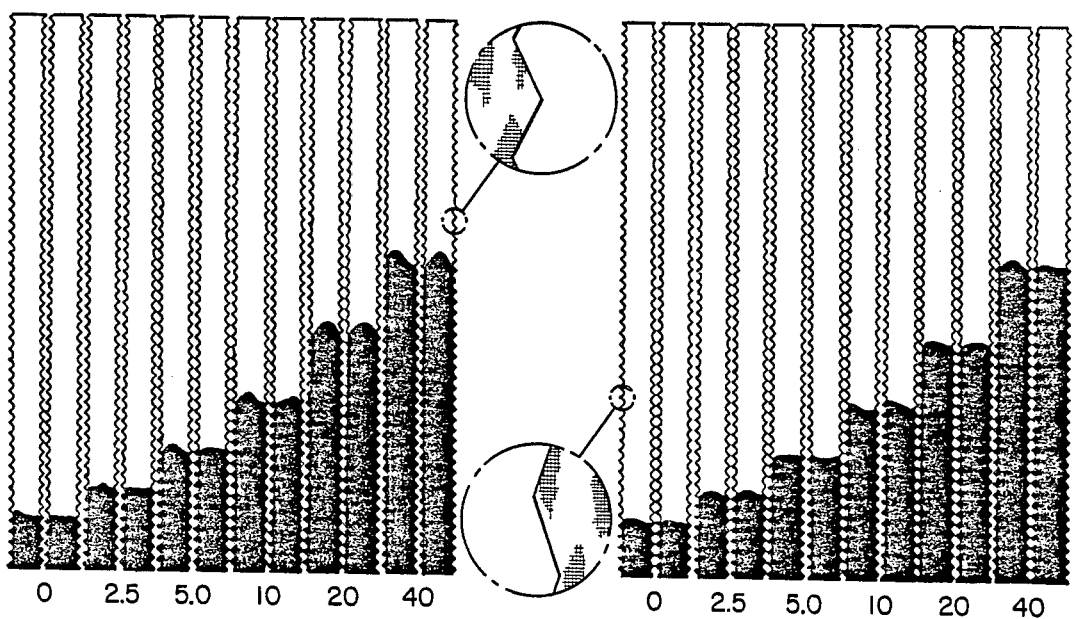

The present invention resides in the discovery of a means of controlling the configuration of the component front of a mixture as it traverses chromatographic material. The portion of the front of such a component near the edge of the chromatographic material generally extends further in the direction of flow of the traversing component than portions that are further from the edge. By employing a device comprised of a chromatographic material having a means for reducing the rate of migration along at least one longitudinal edge, such as for example, a plurality of indentations or a chemical substance, one can control the shape of the front of such component and, for instance, render the front substantially flat or convex.

Before proceeding further, a number of terms will be defined.

"Chromatographic material" means a material susceptible to traversal by a mobile material, either a solvent or a solute, in response to capillary force, gravitational force, electrostatic force, positive pressure, or the like. For the most part, the chromatographic material is a bibulous material which includes inorganic powders such as silica, magnesium sulfate, alumina and the like, natural polymeric materials, particularly cellulosic materials, such as fiber-containing papers, e.g., filter paper, chromatographic paper, etc.; synthetic or modified naturally occurring polymers, such as nitrocellulose, cellulose acetate, poly(vinyl chloride), polyacrylamides, cross-linked dextran, agarose, polyacrylate, etc., either used by themselves or in conjunction with other materials; ion exchange resins; ceramic materials; and the like.

The structure of the chromatographic material may be varied widely and includes fine, medium fine, medium, medium coarse, and coarse. The surface may be varied widely with varying combinations of smoothness and roughness combined with hardness and softness.

"Chromatographic device" means an apparatus comprised of a chromatographic material for use in a chromatographic system. The device may further include a support means for the chromatographic material to maintain such material in a configuration, normally a two dimensional sheet, having at least one longitudinal edge. Exemplary of such support means are glass, Mylar ®, polystyrene, polyethylene, or the like. The particular dimensions and shape of the device will be determined by the chromatographic method in which the device will be employed. The device may be, for example, one or more strips consisting of a layer of chromatographic material on a support.

"Longitudinal edge" means a border of the chromatographic material that is traversed by a component of a mixture during the chromatographic process and is the boundary where the chromatographic material begins or ends. Thus, for example, referring to a rectangular chromatographic strip, the longitudinal edges include all edges that are parallel to the direction of flow of a component and which are in contact with the migrating component.

"Mobile phase" means a medium capable of traversing the chromatographic material. Generally, the mobile phase is a liquid medium, usually a solvent. The liquid medium may contain one or more components or solutes ("traversing components") which may or may not have certain affinity for the chromatographic material. The traversing component may be, for example, an analyte such as a member of a specific binding pair, e.g., hapten, antigen, antibody, and the like.

"Chromatographic strip" means a strip generally prepared from a sheet of chromatographic material of uniform thickness. The strips may have a variety of thicknesses, usually from 0.05 to 2 mm, preferably 0.1 to 0.5 mm, and may vary in shape usually being triangular, rectangular, square, oval, or circular, preferably rectangular. The particular dimensions and shape will be determined by the chromatographic method in which the strips will be employed normally having a maximum width, perpendicular to the flow, of less than 30 cm and a maximum length, parallel to the flow, of less than 40 cm; more frequently a maximum width of 2 cm and a maximum length of 15 cm; preferably a maximum width of 1 cm and a maximum length of 10 cm. Usually, the strip will have two longitudinal edges generally corresponding to the direction of flow of the traversing mobile phase.

"Immunochromatographic method" means a method wherein an antigen or antibody is immobilized on chromatographic material and the complementary binding partner, antibody or antigen, in a liquid medium traverses a chromatographic device.

Exemplary of an immunochromatographic method is the immunoassay disclosed in U.S. Pat. No. 4,168,146. The disclosed method is based on utilizing strips of a porous carrier material having antibodies bound to it. In the method the strips are wetted with an aqueous sample containing the antigen to be quantified. Capillary migration is allowed to take place. The antigen-containing area of the strip is detected by wetting it with antibodies in an aqueous vehicle. The antibodies are normally bound to a signal producing system such as, for example, a water soluble fluorescent color indicating compound or to an enzyme that catalyzes a color-developing reaction.

Another immunochromatographic method is disclosed in U.S. patent application Ser. No. 398,505, filed July 15, 1982, now U.S. Pat. No. 4,435,504. The disclosed method allows detection of an analyte in a sample where a quantitative determination may be readily made without special equipment. The sample is immunochromatographed on a bibulous carrier to which is conjugated a specific binding partner for the analyte. The immunochromatography may be conducted in the presence or absence of a labeled conjugate. The label is a member of an enzymatic signal producing system, which includes one or more enzymes. After chromatographing the samples, if the labeled conjugate was not included in the sample, the chromatograph is contacted with a labeled specific binding pair member which binds to the chromatographic in relation to the distance travelled by the analyte in the sample. By providing appropriate reagents, a product is produced which provides for a detectable signal. In such a case the distance travelled by the analyte may be defined, which distance is related to the amount of analyte in the sample.

"Amplitude" means the distance between the highest point and the lowest point of the indentation, i.e., the depth of the indentations. Referring to FIG. 1, amplitude is represented by the letter "a".

"Wavelength" means the distance between adjacent highest points of the indentations. Referring to FIG. 1, the wavelength is represented by the letter "b."

"In phase" means, when referring to devices having two substantially parallel sets of indentations, that each peak of indentation in one set has a corresponding peak of indentation in the other set such that each pair of corresponding peaks lies substantially on a line perpendicular to the flow of traversing components of the chromatographed mixture. See FIG. 1.

"Out of phase" means, when referring to devices having two substantially parallel sets of indentations, that each peak of indentation in one set has a corresponding valley in the other set such that each pair of peaks and valleys lies substantially on a line perpendicular to the flow of traversing components of the chromatographed mixture. See FIG. 2.

One embodiment of the chromatographic device of the invention is comprised of chromatographic material and has a plurality of indentations. The number, configuration, and dimensions of the indentations are related to the configuration of the front of a component of a mixture traversing the chromatographic material. The longer path created by the indentations results in a retardation of the movement of the components along the edge of the device when compared to the movement of the component along the device lacking such indentations.

The shape of the indentations may vary according to the nature of the device, the chromatographic system, the chromatographic material, the mobile phase, the component, and the like. The indentations may be semi-circular, triangular, rectangular, sinisoidal, cuspid, or combinations thereof, or the like.

Basically, control of the shape of the front of the traversing components may be obtained primarily by selecting certain parameters for the amplitude and wavelength of the indentations. Selection of the appropriate parameters will depend on a number of factors such as, for example, the nature and thickness of the chromatographic material including any support to which the material is attached. If the chromatographic material, including any cuttable support, is to be cut to form the indentations, the nature of the cutting also influences selection of the above parameters.

Generally, the relationship of the above parameters to the configuration of the front of the traversing components may be stated as follows: the greater the amplitude and the shorter the wavelength, the slower the migration of each component near the edge relative to the migration at a distance from the edge along the body of the strip.

The following description is directed to paper cut by either compressive or non-compressive means into strips having a plurality of indentations. This description is by way of illustration and not limitation. Those of ordinary skill in the art having the present disclosure before them will be able to select appropriate parameters for the indentations to be used in conjunction with all devices containing chromatographic material including those wherein the chromatographic device includes a support or chromatography column. The parameters are chosen so that the front of the component is either flat or convex over the portion of the chromatographic material traversed by the component although it is obvious that other shapes could be produced.

Compressive cutting intends any mechanical cutting achieved by means of a blade, wire, or the like. A characteristic of such mechanical cutting is that the edges of the cut material are deformed or compressed. The pores of a bibulous material cut mechanically are compressed near the cut edge when compared to the dimensions of the pores in the body of the strip.

Non-compressive cutting intends a means of cutting the chromatographic material that does not substantially distort the cut edges when compared to edges cut by compressive cutting means. The relationship of the pores within the bibulous material that is cut non-compressively is substantially the same near the cut edges as in the body of the strip. A particular means for achieving non-compressive cutting is a laser beam. The parameters for cutting the bibulous material, such as the intensity of the laser beam, the speed of cutting, and the like will be interdependent and will further depend upon the nature and thickness of the bibulous material. In general, cutting of the bibulous material should be achieved without significant impairment of the bibulous material in the use for which it is intended.

In general, the rate of flow of traversing components will be affected less near the edge of a non-compressively cut chromatographic material than when it is compressively cut. The frequency and size of the indentations for non-compressively cut material will, therefore, generally be less than for compressive cutting. For analytical applications paper strips will have a width of from about 3 to 30 mm and a thickness of from about 0.1 to 2 mm. The amplitude for the indentations will be from about 0.3 to 10 mm and the wavelength will be from about 0.2 to 5 mm, more usually the amplitude will be from about 0.5 to 3 mm and the wavelength will be from about 0.5 to 2 mm.

The exact dimensions of the indentations will depend on the shape of the indentations. The main consideration is that the greater the increase in length of the edge caused by the indentations, the slower will be the flow of the traversing component.

It is within the scope of the present invention to use more than one set of parameters for the indentations on each particular device. For example, FIG. 4 depicts a paper strip having a set of indentations at its bottom portion which differ from those at its top portion. Thus, by employing more than one set of parameters for the indentations, more versatility can be achieved in controlling the shape of the front of the traversing component.

The devices of the present invention find particular use in affinity chromatographic methods, especially immunochromatographic methods. The present invention, therefore, comprises a diagnostic device for use in such methods. The diagnostic device comprises a bibulous material and at least one non-diffusively bound member of a specific binding air ("mip"). The device may also include one or more members of a signal producing system. Generally the analyte to be measured is a mip selected from the group consisting of ligand and receptor. The ligand and receptor are related in that the receptor specifically binds to a polar and spacial organization of the ligand, being able to distinguish the ligand from other compounds having similar characteristics. The signal producing system member may be, for example, an enzyme or a chromophore such as a fluorescent compound. Generally, a plurality of mips are attached to the bibulous material.

The diagnostic device may take the form of an immunochromatographic strip wherein the bibulous material is paper. The thickness of the immunochromatographic strip will generally vary from about 0.05 mm to about 2 mm, more usually being about 0.1 mm to 0.5 mm, preferably from about 0.2 mm to about 0.4 mm. Usually, the strip will have a width of from about 2 to 12 mm, preferably from about 3 to 8 mm, and will have a length of from about 20 to 250 mm, preferably from about 30 to 150 mm.

Methods for binding a wide variety of materials to a bibulous material, e.g., cellulose, are found in the literature. See for example, U.S. Pat. No. 4,168,146. The amount of a mip which is bound to the bibulous material will vary depending upon the size of the diagnostic device and the affinity chromatographic method in which the device is used and the amount required to bind the homologous mip. Generally, for an affinity chromatographic strip, the amount of mip will range from about $10^{-5}$ to $10^{-15}$ moles per square centimeter, more usually from about $10^{-7}$ to $10^{-12}$ moles per square centimeter. The number of moles per unit area will be varied in order to insure that there is sufficient modulation of the distance traversed by the traversing component along the affinity chromatographic strip within the concentration range of interest.

A particular advantage of the device of the present invention is realized in the use of the device in immunochromatography wherein the mips are selected from the group consisting of antigen and antibody. We have found that the sensitivity as well as the accuracy of the immunochromatographic test is enhanced. While enhanced accuracy is expected, the enhanced sensitivity is unexpected. Enhanced accuracy in the test results from a more defined front of the traversing component so that one may more readily determine the distance of travel of the component. Enhancement in sensitivity means that the migration distance of the traversing component obtained for a given concentration of an analyte is greater when the present device is employed in an immunochromatographic test compared to when a conventional device is used. The enhanced sensitivity which is realized in the use of the present device is surprising and unexpected.

In another embodiment of a chromatographic device in accordance with the present invention, the means for controlling the shape of the front of the traversing component is a chemical treatment wherein a chemical substance capable of reducing the migration of the traversing component along the treated edge, such as a hydrophobic or polymeric material, is deposited along the the longitudinal edge. The chemical substance may be a prepolymer which is contacted with, and polymerized along, the longitudinal edge. The polymer may be either synthetic or natural, including, for example, waxes such as paraffins, etc., elastomers such as silicone rubber, polyesters such as cellulose acetate, etc., polyamides, polyacrylates, and the like. The chemical substance in a suitable carrier is applied uniformly to the longitudinal edge of the chromatographic material. Application of the chemical substance may be carried out by spraying or brushing the longitudinal edge with the substance, dipping the edge in the substance, or the like. It is also possible to chemically treat the chromatographic material in a narrow band area where a longitudinal edge will subsequently be formed.

The amount of the chemical substance to be applied will be sufficient to obtain control of the shape of the front of a traversing component. Thus, the amount should be sufficient to retard the migration of the traversing component along the longitudinal edge when compared to the migration of such component along an untreated edge. The amount of the substance to be applied will depend on the nature, including porosity, of the chromatographic material, the nature of the chemical substance used, and the like. Generally, the chromatographic material will be saturated with the chemical substance. For paper strips, about 30 to 98% (by weight) of the chemical substance deposited on the longitudinal edge will provide the appropriate control although as little as 1% of a non-wettable surfactant may be used.

The longitudinal edge should be treated with the chemical substance at a sufficient distance inward to reduce the accelerated migration of the traversing component, which results from compression of the edges in standard cutting techniques. Optimally, the edge treatment should be such that the untreated portion of the chromatographic material has substantially the same pore size throughout. For paper strips having a width of about 3-30 mm and a thickness of about 0.1-2 mm, the chemical treatment should extend a distance inward from the longitudinal edge of from about 0.3-10 mm.

The following examples are offered by way of illustration and not by way of limitation.

The following abbreviations are used hereafter: HRP—horse radish peroxidase; NHS-N-hydroxy succinimide; EDAC-ethyl dimethylaminopropyl carbodiimide; DMF-dimethyl formamide; BSA-bovine serun albumin. Temperatures not otherwise indicated are Celsius, while parts are by weight except for mixtures of liquids which are by volume.

EXAMPLE 1

Preparation of Immunochromatographic Sheets

A sheet of Whatman 31 ET of about 550 cm$^2$ was immersed in 1.8 l. CH$_2$Cl$_2$, 0.2M in carbonyldiimidazole, and the mixture gently stirred for one hour at room temperature. Additional sheets were activated in the same activating solution. Each sheet was then washed with 300 ml CH$_2$Cl$_2$ and air dried with an air gun over about 20 sec. The sheet was then immersed in a solution of 500 μl of a 49 mg/ml solution of antitheophylline, and 200 ml of buffer 0.1M sodium phosphate, pH 7.0, 0.2M NaCl and the mixture was mildly shaken for 4 hours at room temperature. After washing with the phosphate buffer, the solution was then immersed in 4% aqueous Dextran T10 solution to serve as a preservative, followed by blotting the sheet, freezing and lyophilizing.

EXAMPLE 2

Preparation of Immunochromatographic Strips

A Coherent Model 42, CO$_2$ laser at 50 watts CW (from Coherent, Inc., Palo Alto) and an Anomatic II CNC X-Y table were employed. A Coherent Model 303 coaxial gas jet was used at an air pressure of 60 psig. A standard cutting box was used.

The cutting box was placed on the X-Y table and a sheet of plexiglass was placed on the cutting box. A narrow slot was cut in the plexiglass using the laser beam. An immunochromatographic sheet prepared in Example 2 was placed over the plexiglass. The sheet was cut into strips which were 4.5 mm wide and 90 mm in length. A cutting speed of 19 centimeters per second was employed. The sheets were cut to give groups of strips, wherein the phase, amplitude and period of the indentations along the edge of the strip in each individual group was as indicated in the table in Example 6. For the groups of FIGS. 5–10, the indentations were triangular in shape; for the group of FIG. 11, the indentations were semi-circular in shape.

EXAMPLE 3

Preparation of HRP-Oxyamine

To 5 ml of 10 mg/ml horse radish peroxidase in 5 mM sodium acetate, pH 4.5 buffer, was added 50 μl 0.2M sodium periodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° C. and 2.9 ml of 0.2M 2,2'-oxy-bis-ethylamine in 0.5M carbonate buffer, pH 9.5, at 4° added. The pH of the mixture was adjusted to 9.5 with 1N sodium hydroxide, stirred for 2 hrs and 3.52 ml of a 4 mg/ml sodium borohydride-water solution added and the mixture allowed to react for 3 hr, followed by chromatography through a Sephadex G-50 column.

The above procedure was repeated using 400 mg of HRP and 3.5 g of 2,2'-oxy-bis-ethylamine. No significant change in enzyme activity was observed between the native amine and the modified amine, which has about four additional amino groups.

EXAMPLE 4

Conjugation of Theophylline and HRP

Into a reaction flask was introduced 8.1 mg of 1-methyl-3-(3'-carboxypropyl)xanthine, 3.8 mg of NHS, 6.7 mg EDAC and 125 μl DMF and the mixture allowed to stand overnight at room temperature.

To four 1.3 ml samples of HRP-oxyamine (1 mg) from Example 3 in 0.1M sodium carbonate, pH 9.0 was added varying amounts of the ester prepared above to provide for preparations having mole ratios of theophylline to HRP of 400; 200, and two of 100 each. Into the first reaction mixture (400 mole ratio) was added 0.217 ml of DMF and 66 μl of the above ester in 8.25 μl increments over a period of about 2 hrs. Into the second reaction mixture (200 mole ratio), 0.238 ml of DMF was added and 33 μl of the ester added incrementally in 8.25 μl increments. Into the third reaction mixture (100 mole ratio), 0.24 ml of DMF was added and 16.5 μl of the ester added in 8.2 μl increments, while in the final reaction mixture (100 mole ratio), no DMF was added, and 8.25 μl of the ester was added in 2.1 μl increments. During the addition, the temperature was maintained at 4°, and the mixture then allowed to stand overnight at 4°.

The reaction mixtures were then worked up by chromatography on G-25 Sephadex ® with standard buffer. Folin and UV spectroscopic analysis indicated theophylline/HRP ratios of 6.9, 4.0, 1.6 and 2.1, respectively.

EXAMPLE 5

Immunochromatographic Assay

In carrying out the assay, the strips prepared in Example 2 were employed. Samples containing 0, 2.5, 5.0, 10, 20 and 40 μg/ml (10 μl) were mixed with a 0.5 ml of a solution containing 0.1M NaH$_2$PO$_4$, 0.2M NaCl, pH 7.0, 1 mg/ml BSA, 0.05% Triton QS-15, 100 μg/ml glucose oxidase (Sigma, E.C. 1.1.3.4), and 0.2 μg/ml HRP-theophylline conjugate. The end of a strip was dipped into this mixture. After the solution had reached the top of the strip by capillary migration (6–12 min), the strip was removed from the enzyme solution and was totally immersed in a development solution comprising 15 ml of 50 mM glucose and 200 μg/ml of 4-chloro-1-naphthol and allowed to stand for 20 min. The results are depicted in FIGS. 5–11.

Figure 12:
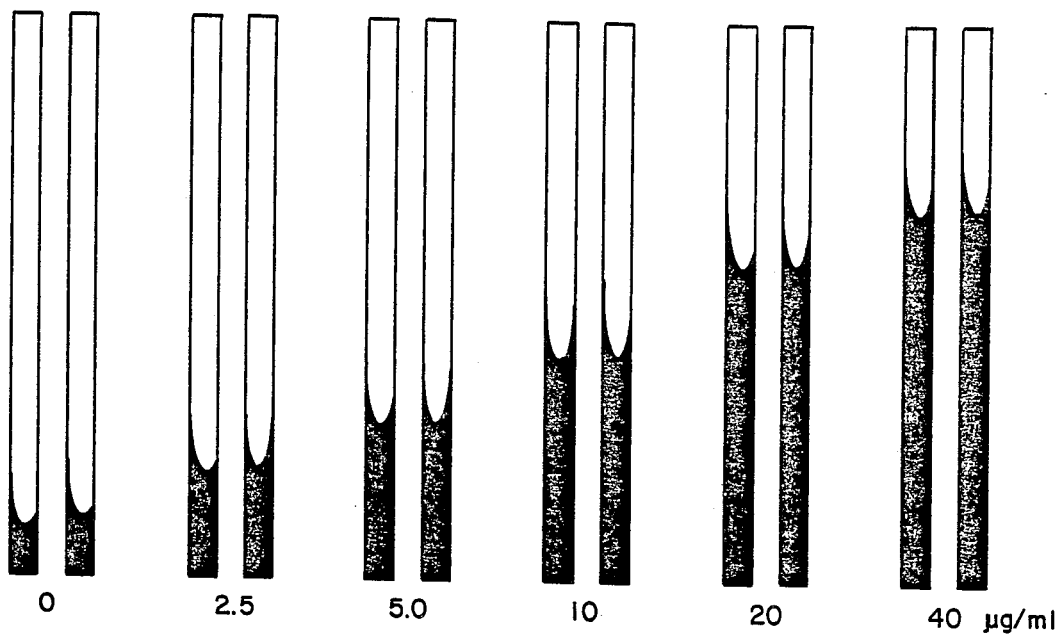
FIG. 12 depicts the results of an immunochromatographic assay wherein the chromatographic devices are mechanically cut from sheets of chromatographic material by means of a slitter.
Figure 13:
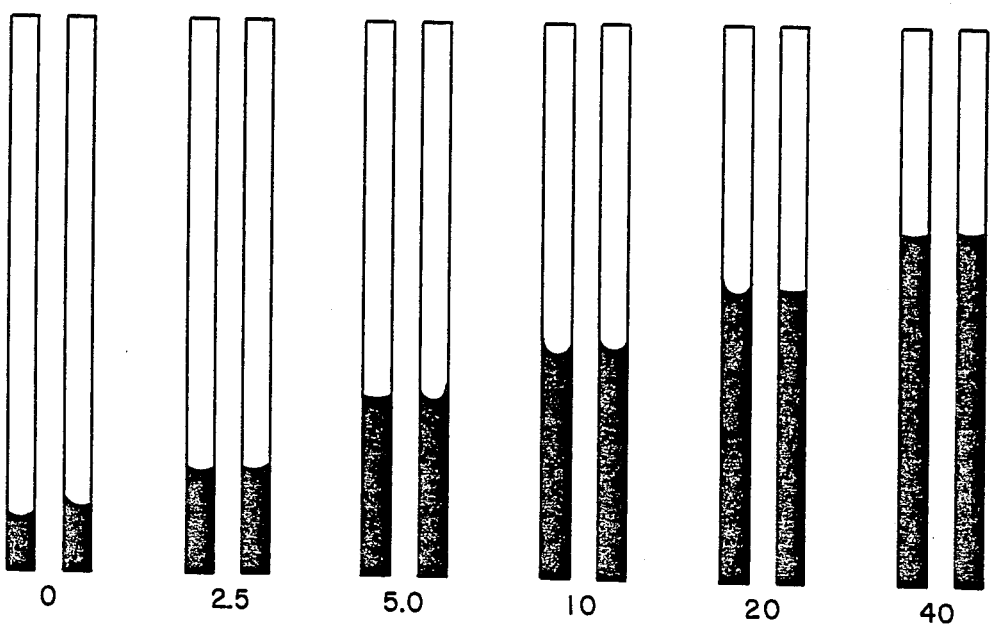
FIG. 13 depicts the results of an immunochromatographic assay wherein the chromatographic devices are cut from sheets of a chromatographic material by means of a laser beam.

For purposes of comparison assays were also conducted employing immunochromatographic strips prepared from the sheet of Example 2 by cutting the sheets with a slitter or with a laser. The results are shown in FIGS. 12 and 13, respectively.

The following table summarizes important parameters:

| Group (FIG.) | Phase | Amplitude (mm) | Wavelength (mm) |
| --- | --- | --- | --- |
| 5 | in | 0.25 | 0.5 |
| 6 | in | 0.5 | 1 |
| 7 | out | 0.5 | 2.0 |
| 8 | out | 0.5 | 3.0 |
| 9 | in | 1 | 1 |
| 10 | in | 1.5 | 1 |
| 11 | in | 0.5 | 1 |
| 12 (control) | — | — | — |
| 13 (control) | — | — | — |

FIGS. 5–11 show that the front of the traversing component of the sample produced on strips cut in accordance with the invention is substantially flat or convex along the portion of the strip traversed by the component. It is further evident that the front becomes more convex as the amplitude of the indentations is increased.

Referring to FIG. 12 it can be seen that the slitter cut strips exhibit extensive concavity of the meniscus resulting from accelerated traversal of the component of the sample along the longitudinal edges of the strip when compared to the rate of traversal of the liquid sample along the body of the strip.

FIG. 13 shows that the accelerated traversal of the component along the longitudinal edges of the strips cut with a laser has been reduced when compared to the rate of traversal of the liquid sample along the body of the strip.

Figure 14:
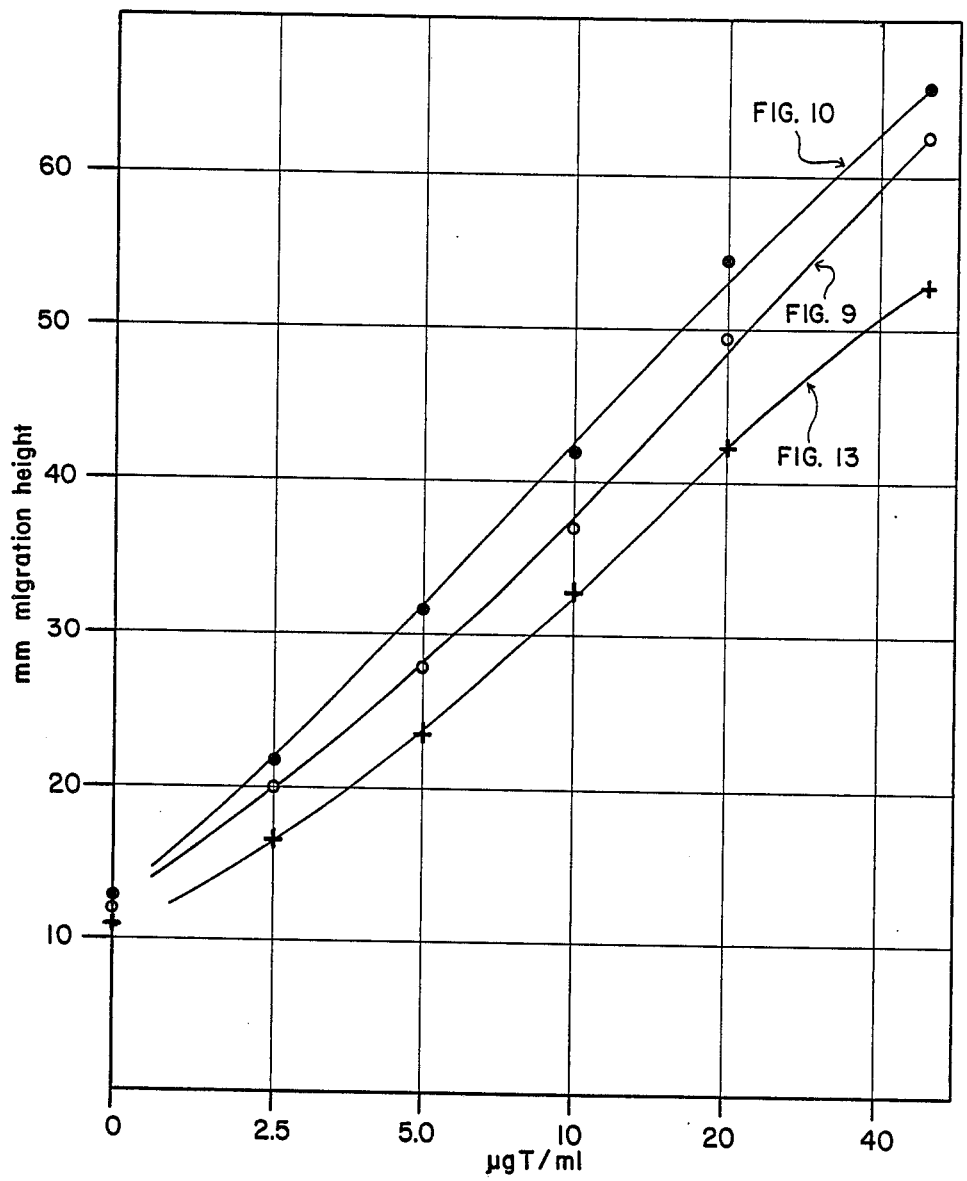
FIG. 14 is a graphic depiction of the enhanced response obtained in the immunochromatographic assay of FIGS. 9 and 10 compared to results of the assay of FIG. 13. The x-axis is the $\mu g$ of theophylline/ml of the assay sample and the y-axis is the mm migration height of the theophylline on the chromatographic devices.

FIG. 14 depicts a graphic comparison between the level of response (mm migration height) between strips prepared in accordance with the present invention (strips of FIGS. 9 and 10) and strips cut from a sheet by means of a laser but not including indentations (strips of FIG. 13). As can be seen, the strips of the invention exhibited an enhanced response (greater migration height) when compared to strips not in accordance with this invention. All strips contained the same level of antibody. This increased sensitivity is unexpected.

EXAMPLE 6

Preparation of paper Strip Having Chemically Treated Edges

Twelve strips prepared in accordance with Example 2 were held together face to face. Krylon ® acrylic spray (No. 1303 from Borden, Inc., Columbus, Ohio) was sprayed along the longitudinal edges of the strips. The strips were allowed to dry.

EXAMPLE 7

Immunochromatographic Assay Employing Paper Strips Having Chemically Treated Edges The assay procedure set forth in Example 5 was followed using the strips of Example 6. The results are depicted in FIG. 15.

Figure 15:
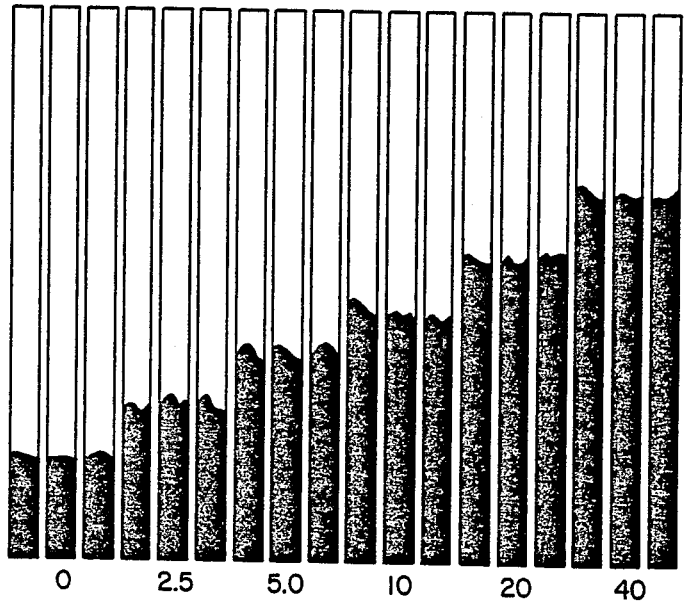
FIG. 15 depicts the results of immunochromatographic assays employing chromatographic devices in accordance with another embodiment of the present invention.

FIG. 15 shows that the front of the traversing component of the sample produced on strips whose edges have been chemically treated in accordance with the present invention is substantially flat or slightly convex along the portion of the strip traversed by the component.

What is claimed is:

1. A device for use in a chromatographic system wherein a component of a mixture is partitioned between a liquid phase and an immobile phase, said device being comprised of a chromatographic material having a longitudinal edge, wherein in said system said component traverses at least a portion of said chromatographic material and said longitudinal edge includes means for controlling the shape of the front of the traversing component.

2. The device of claim 1 wherein said means render the shape of said front substantially flat or convex, when considered perpendicular to the direction of traversal of said component.

3. A device for use in a chromatographic system wherein a component of a mixture is partitioned between a liquid phase and an immobile phase, said device being comprised of a chromatographic material having a longitudinal edge, wherein in said system said component traverses at least a portion of said chromatographic material and said longitudinal edge includes means comprising a plurality of indentations for controlling the shape of the front of the traversing component.

4. A device for use in a chromatographic system wherein a component of a mixture is partitioned between a liquid phase and an immobile phase, said device being comprised of a chromatographic material having a longitudinal edge, wherein in said system said component traverses at least a portion of said chromatographic material and said longitudinal edge includes means comprising a chemical substance capable of reducing the rate of migration of said traversing component along said edge for controlling the shape of the front of the traversing component.

5. The device of claim 1 wherein the chromatographic material is a strip of bibulous material.

6. The device of claim 1 wherein a member of a specific binding pair is non-diffusively bound to the chromatographic material.

7. An immunochromatographic device comprising the device of claim 6 wherein the member of the specific binding pair is an antigen or an antibody.

8. The immunochromatographic device of claim 7 wherein a member of a signal producing system is bound to said chromatographic material.

9. The immunochromatographic device of claim 7 wherein the member of a signal producing system is an enzyme.

10. The immunochromatographic device of claim 6 wherein the signal producing system comprises two enzymes which are related by the product of one enzyme being a substrate for the other enzyme.

11. A device for use in a chromatographic system wherein a component of a mixture is partitioned between a liquid phase and an immobile phase, said device being comprised of a chromatographic material and having a plurality of indentations along a longitudinal edge, the number, dimensions, and configuration of said indentations being sufficient to render the front of said traversing component substantially flat or convex.

12. The device of claim 11 wherein the indentations have an amplitude which affects the configuration of the front in that the greater the amplitude, the less the migration of a traversing component near a longitudinal edge relative to migration away from the edge.

13. The device of claim 12 wherein the strip has a thickness of from about 0.1 to 2 mm and a width of from about 3 to 30 mm and the amplitude of the indentations is from about 0.3 to 10 mm.

14. The device of claim 11 wherein a member of a specific binding pair is non-diffusively bound to the chromatographic material.

15. The device of claim 14 wherein a member of a signal producing system is bound to the chromatographic material.

16. The device of claim 15 wherein the member of the signal producing system is an enzyme.

17. The device of claim 15 wherein the signal producing system comprises two enzymes which are related by the product of one enzyme being a substrate for the other enzyme.

18. A diagnostic kit, for conducting an immunochromatographic assay, which comprises in packaged combination
    (a) the device of claim 1, and
    (b) a member of said specific binding pair conjugated to a member of a signal producing system.

19. A device for for use in a chromatographic system wherein a component in a liquid medium traverses at least a portion of said device, said device comprising at least one strip of a porous material, said strip having two longitudinal edges, said longitudinal edges having a plurality of indentations, the number, configuration, and dimensions of said indentations being sufficient to render the configuration of the front of said traversing component substantially flat or convex.

20. The device of claim 19 wherein the indentations are triangular or semi-circular in shape and have an amplitude which affects the configuration of the front in that the greater the amplitude, the less the migration of the traversing component near the longitudinal edge relative to migration away from the edge.

* * * * *